United States Patent
Young et al.

(10) Patent No.: US 9,937,204 B2
(45) Date of Patent: Apr. 10, 2018

(54) METHOD AND COMPOSITION FOR PREVENTION AND TREATMENT OF ORAL FUNGAL INFECTIONS

(71) Applicant: Micropure, Inc., Scottsdale, AZ (US)

(72) Inventors: Elena J. Young, Scottsdale, AZ (US); James L. Ratcliff, Pueblo West, CO (US)

(73) Assignee: MICROPURE, INC., Scottsdale, AZ (US)

( * ) Notice: Subject to any disclaimer, the term of this patent is extended or adjusted under 35 U.S.C. 154(b) by 0 days.

(21) Appl. No.: 15/475,006

(22) Filed: Mar. 30, 2017

(65) Prior Publication Data

US 2017/0216351 A1    Aug. 3, 2017

Related U.S. Application Data

(63) Continuation of application No. 12/500,163, filed on Jul. 9, 2009, now abandoned.

(60) Provisional application No. 61/079,532, filed on Jul. 10, 2008.

(51) Int. Cl.
| | |
|---|---|
| A61K 33/00 | (2006.01) |
| A61P 31/04 | (2006.01) |
| A61K 33/20 | (2006.01) |
| A61K 9/00 | (2006.01) |

(52) U.S. Cl.
CPC ............ *A61K 33/20* (2013.01); *A61K 9/0053* (2013.01)

(58) Field of Classification Search
CPC .................................................... A61K 33/16
See application file for complete search history.

(56) References Cited

U.S. PATENT DOCUMENTS

| | | |
|---|---|---|
| 2,451,897 A | 10/1948 | Woodward |
| 2,482,891 A | 9/1949 | Mathieson |
| 3,271,242 A | 9/1966 | McNicholas et al. |
| 4,084,747 A | 4/1978 | Alliger |
| 4,330,531 A | 5/1982 | Alliger |
| 4,499,077 A | 2/1985 | Stockel et al. |
| 4,552,679 A | 11/1985 | Schobel et al. |
| 4,689,215 A | 8/1987 | Ratcliff |
| 4,696,811 A | 9/1987 | Ratcliff |
| 4,786,492 A | 11/1988 | Ratcliff |
| 4,788,053 A | 11/1988 | Ratcliff |
| 4,792,442 A | 12/1988 | Ratcliff |
| 4,793,989 A | 12/1988 | Ratcliff |
| 4,808,389 A | 2/1989 | Ratcliff |
| 4,818,519 A | 4/1989 | Ratcliff |
| 4,837,009 A | 6/1989 | Ratcliff |
| 4,851,213 A | 7/1989 | Ratcliff |
| 4,855,135 A | 8/1989 | Ratcliff |
| 4,861,514 A | 8/1989 | Hutchings |
| 4,886,657 A | 12/1989 | Ratcliff |
| 4,889,714 A | 12/1989 | Ratcliff |
| 4,891,216 A | 1/1990 | Kross et al. |
| 4,902,498 A | 2/1990 | Agricola et al. |
| 4,925,656 A | 5/1990 | Ratcliff |
| 4,963,346 A | 10/1990 | Amer |
| 4,975,285 A | 12/1990 | Ratcliff |
| 5,200,171 A | 4/1993 | Ratcliff |
| 5,281,412 A | 1/1994 | Lukacovic et al. |
| 5,348,734 A | 9/1994 | Ratcliff |
| 5,489,435 A * | 2/1996 | Ratcliff ................. A61K 8/20 424/422 |
| 5,618,550 A | 4/1997 | Ratcliff |
| 5,667,817 A | 9/1997 | Kross |
| 5,707,975 A | 1/1998 | Francois et al. |
| 5,738,840 A | 4/1998 | Richter |
| 5,772,986 A | 6/1998 | Kross |
| 6,077,502 A | 6/2000 | Witt et al. |
| 6,132,702 A | 10/2000 | Witt et al. |
| 6,136,348 A | 10/2000 | Ratcliff et al. |
| 6,231,830 B1 | 5/2001 | Madray |
| 6,235,269 B1 | 5/2001 | Witt et al. |
| 6,251,372 B1 | 6/2001 | Witt et al. |
| 6,264,924 B1 | 7/2001 | Witt et al. |
| 6,280,775 B1 | 8/2001 | Sasson et al. |
| 6,325,997 B1 | 12/2001 | Christopfel |
| 6,350,438 B1 | 2/2002 | Witt et al. |
| 6,375,933 B1 | 4/2002 | Subramanyam |
| 6,582,682 B2 | 6/2003 | Stier |
| 6,696,047 B2 | 2/2004 | Scott et al. |
| 6,780,838 B2 | 8/2004 | Lipton et al. |
| 7,387,774 B2 | 6/2008 | Faller et al. |
| 7,737,166 B2 * | 6/2010 | Kawakami ........... C07D 263/56 514/210.21 |

(Continued)

FOREIGN PATENT DOCUMENTS

| | | |
|---|---|---|
| WO | 0613678 | 9/1994 |
| WO | 2003022256 | 3/2003 |
| WO | 2009009163 | 1/2009 |

OTHER PUBLICATIONS

Pfaller et al., "Epidemiology of Invasive Candidiasis: a Persistent Public Health Problem." Clinical Microbiology Reviews, Jan. 2007, vol. 20, No. 1, p. 133-163.*
Li et al., "Candida glabrata, an Emerging Oral Opportunistic Pathogen." J Dent Res 86(3):204-215,2007.*
Restriction Requirement dated Dec. 28, 2010 in U.S. Appl. No. 12/500,163.
Office Action dated Jan. 27, 2011 in U.S. Appl. No. 12/500,163.
Office Action dated May 26, 2011 in U.S. Appl. No. 12/704,360.
Final Office Action dated Oct. 19, 2011 in U.S. Appl. No. 12/500,163.

(Continued)

*Primary Examiner* — Walter Webb
(74) *Attorney, Agent, or Firm* — Snell & Wilmer LLP

(57) ABSTRACT

A composition of stabilized chlorine dioxide at a concentration range of about 0.0004% to about 0.8% (w/v) having anti fungal properties to prevent oral fungal infections and method of use are disclosed.

2 Claims, No Drawings

(56) References Cited

U.S. PATENT DOCUMENTS

| | | | |
|---|---|---|---|
| 8,252,771 B2* | 8/2012 | Utecht | A61K 9/0048 514/23 |
| 2002/0028324 A1 | 3/2002 | Koichi et al. | |
| 2002/0197215 A1 | 12/2002 | Stier | |
| 2003/0129144 A1 | 7/2003 | Scott | |
| 2007/0190176 A1* | 8/2007 | Percival | A01N 37/44 424/618 |
| 2008/0055154 A1 | 3/2008 | Martucci et al. | |
| 2010/0009009 A1 | 1/2010 | Young et al. | |
| 2010/0233101 A1 | 9/2010 | Grootveld et al. | |
| 2011/0318282 A1 | 12/2011 | Ratcliff et al. | |
| 2012/0164084 A1 | 6/2012 | Ratcliff et al. | |
| 2015/0017107 A1 | 1/2015 | Hill | |

OTHER PUBLICATIONS

Final Office Action dated Dec. 2, 2011 in U.S. Appl. No. 12/704,360.
Advisory Action dated Mar. 5, 2012 in U.S. Appl. No. 12/500,163.
Office Action dated Dec. 19, 2012 in U.S. Appl. No. 12/704,360.
Restriction Requirement dated Mar. 28, 2013 in U.S. Appl. No. 13/131,506.
Restriction Requirement dated Apr. 22, 2013 in U.S. Appl. No. 13/131,506.
Final Office Action dated Aug. 26, 2013 in U.S. Appl. No. 12/704,360.
Office Action dated Jan. 24, 2014 in U.S. Appl. No. 12/500,163.
Advisory Action dated Feb. 12, 2014 in U.S. Appl. No. 12/704,360.
Office Action dated Apr. 10, 2014 in U.S. Appl. No. 12/704,360.
Office Action dated May 22, 2014 in U.S. Appl. No. 13/131,506.
Final Office Action dated Jul. 31, 2014 in U.S. Appl. No. 12/500,163.
Final Office Action dated Oct. 22, 2014 in U.S. Appl. No. 12/704,360.
Advisory Action dated Nov. 13, 2014 in U.S. Appl. No. 12/500,163.
Advisory Action dated Mar. 6, 2015 in U.S. Appl. No. 12/704,360.
Office Action dated Mar. 12, 2015 in U.S. Appl. No. 12/500,163.
Office Action dated Jun. 18, 2015 in U.S. Appl. No. 12/704,360.
Final Office Action dated Aug. 6, 2015 in U.S. Appl. No. 12/500,163.
Restriction Requirement dated Oct. 8, 2015 in U.S. Appl. No. 14/145,426.
Advisory Action dated Nov. 13, 2015 in U.S. Appl. No. 12/500,163.
Final Office Action dated Dec. 10, 2015 in U.S. Appl. No. 12/704,360.
Final Office Action dated Dec. 17, 2015 in U.S. Appl. No. 13/131,506.
Office Action dated Jan. 29, 2016 in U.S. Appl. No. 12/500,163.
Office Action dated Mar. 24, 2016 in U.S. Appl. No. 12/704,360.
Advisory Action dated Apr. 21, 2016 in U.S. Appl. No. 13/131,506.
Office Action dated May 20, 2016 in U.S. Appl. No. 14/145,426.
Final Office Action dated Sep. 30, 2016 in U.S. Appl. No. 12/500,163.
Final Office Action dated Nov. 25, 2016 in U.S. Appl. No. 12/704,360.
Office Action dated Dec. 23, 2016 in U.S. Appl. No. 13/131,506.
Abu-Elteen K.H., et al., The prevalence of Candida albicans populations in the mouths of complete denture wearers, Microbiologica, 21, pp. 41-48 (1998).
Aoba, T., et al., Dental Fluorosis: Chemistry and Biology, Critical Reviews in Oral Biology & Medicine, 13, pp. 155-170 (2002).
Bagg J., et al.., Voriconazole susceptibility of yeasts isolated from the mouths of patients with advanced cancer. Journal of Medical Microbiology, 54, pp. 959-964 (2005).
Barkvoll et al., Interaction Between Chlorhexidine Digluconate and Sodium Monofluorophosphate in Vitro, Scand. J. Dent. Res., 96(1), abstract (1 page) (1988).
Benarde et al., Kinetics and Mechanism of Bacterial Disinfection by Chlorine Dioxide, Applied Microbiology, vol. 15, No. 2, pp. 257-265 (1967).
Berg J.D., et al.., Effect of chlorine dioxide on selected membrane functions of *Escherichia coli*, Journal of Applied Bacteriology, 60, pp. 213-220 (1986).
Blignaut, E., Oral candidiasis and oral yeast carriage among institutionalized South African paediatric HIV/AIDS patients, Mycopathologia, 163, pp. 67-73 (2007).
Bouillaguet S., Biological Risks of Resin-Based Materials to the Dentin-Pulp Complex, Critical Reviews in OralBiology & Medicine,15(1), pp. 47-60 (2004).
Braly A. et al., The Effect of Prism Orientation in the Indentation Testing of Human Molar Enamel, Arch. Oral Biol., 52(9), pp. 856-860 (2007).
Brand H.S., et al., Effect of a protein-rich meal on urinary and 2 salivary free amino acid concentrations in human subjects, Clinica Chimica Acta, 264; 37-47, abstract (1 page) (1997).
Campisi G., et al., Candidal carriage in the oral cavity of human immunodeficiency virus-infected subjects, Oral Surgery Oral Medicine Oral Pathology Oral Radiology and Endodontics, 93, pp. 281-286 (2002).
Canton E., et al., Minimum fungicidal concentrations of amphotericin B for bloodstream *Candida* species, Diagnostic Microbiology and Infectious Disease, 45, pp. 203-206 (2003).
Cartledge M.D., et al., Non-albicans oral candidiasis in HIV-positive patients, Journal of Antimicrobial Chemotherapy, 43, pp. 419-422 (1999).
Cate, et al., Molecular and Cellular Mechanisms That Lead to Candida Biofilm Formation, J Dental Research, 88 (2), pp. 105-115 (2009).
Challacombe S.J., Immunologic aspects of oral candidiasis, Oral Surgery Oral Medicine Oral Pathology, 78, pp. 202-210 (1994).
Chang H., et al., High-resolution 1 H NMR investigations of the oxidative consumption of salivary biomolecules by oral rinse peroxides, Acta Odontologia Scandanivica (in press), abstract (1 page) (2012).
Chang H., et al., 1H NMR investigations of the molecular4 nature of cobalt(II) ions in human saliva, Archives of Biochemistry and Biophysics, 520, (Abstract) 1 page (2012).
Chapek, et al., Management of Periodontitis with Oral-Care Products, Compend. Cantin. Educ Dent, vol. XV, No. 6, 4 pgs (1994).
Worthington H.V., et al,. Interventions for treating oral candidiasis for patients with cancer receiving treatment (Review), Cochrane Database of Systemic Reviews, Issue 2. Art. No. CD001972. DOI:10.1002/14651858. CD001972. pub3, 6 pgs, (2007).
Yu, D., et al., Caries Inhibition Efficacy of an Antiplaque/ Antigingivitis Dentifrice; Am.Jour.Dent, 14, pp. 14C-17C (2000).
Zero, D.T., Dentifrices, Mouthwashes, and Remineralization/Caries Arrestment Strategies; BMC Oral Health, 6 (Suppl I):S9, 13 pgs (2006).
Chattopadhyay A., et al., Risk indicators for HIV-associated jointly occurring oral candidiasis and oral hairy leukoplakia, AIDS Patient Care and STDs, 21 (11), pp. 825-832 (2007).
Chattopadhyay A., et al., Risk indicators for oral candidiasis and oral leukoplakia, HIV-infected adults. Community Dentistry and Oral Epidemiology, 33, pp. 35-44 (2005).
Chattopadhyay A., et al. Incidence of oral candidiasis and oral hairy leukoplakia in HIV-infected adults in North Carolina, Oral Surgery Oral Medicine Oral Pathology Oral Radiology and Endodontics, 99, pp. 39-47 (2005).
Chinake, et al., Oxidation of formaldehyde by chlorite in basic and slightly acidic media. Journal of Physical Chemistry, vol. 102, pp. 606-611, (1998).
Chinake, et al., Oxyhalogen-Sulfur Chemistry: Oxidation of Taurine by Chlorite in Acidic Medium, Jounral of Physical Chemistry, 101, pp. 1207-1214 (1997).
CLSI, Reference Method for Broth Dilution Antifungal Susceptibility Testing of Yeasts; Approved Standard—Second11 Edition, CLSI document M27-A2 (ISBN 1-56238-469-4), CLSI, 940 West Valley Road, Suite 1400, Wayne, PA 19087-1898 USA, 15 pgs (2002).
Coleman et al., Candidiasis: the emergence of a novel species, Candida dubliniensis, AIDS, vol. 11, No. 5, pp. 557-567, (1997).

(56) References Cited

OTHER PUBLICATIONS

Conley L.J., et al., The association between cigarette smoking and selected HIV-related medical conditions, AIDS, 10, pp. 1121-1126 (1996).
Coogan, et al., (B1) Candida and Mycotic Infections, Advances in Dental Research, No. 19, pp. 130-138 (2006).
Cury J. et al., Enamel Remineralization: Controlling the Caries Disease or Treating Early Caries Lesions?, Braz. OralRes., 23 Spec.Issue 1; pp. 23-30 (2009).
Cury J. et al., How to Maintain a Cariostatic Fluoride Concentration in the Oral Environment, Advances in DentalRes., 20; pp. 13-16 (2008).
Darkwa, et al., Oxyhalogen-Sulfur Chemistry: Oxidation of N-Acetylcysteine by Chlorite and Acidic Bromate, The Journal of Physical Chemistry A., vol. 107, No. 46, pp. 9834-9845 (Nov. 1, 2003).
Davies A.N., et al., Oral candidosis in patients with advanced cancer, Oral Oncology, 42, pp. 698-702 (2006).
Denes, G. et al., Oxidation of SnF2 Stannous Fluoride in Aqueous Solutions, Hyperfine Interactions, vol. 90,No. 1, 2 pgs (1994).
Edgar W.M., et al., Role of Saliva in Caries Models, Advances in Dental Res., 9(3); pp. 235-238 (1995).
Emilson, C.G., et al., Effect of a Fluoride-Containing Chlorhexidine Gel on Bacteria in Human Plaque, Scand.J. Dent. Res., 84(2), abstract (1 page) (1976).
European Commission, Enterprise Directorate-General, The Rules Governing Cosmetic Products in the European Union,Cosmetics Legislation,—Cosmetic products, 1999 Edition, vol., 1, 3 pgs (1999).
Featherstone, J.D.B., Caries Prevention and Reversal Based on the Caries Balance, Pediatric Dentistry, 28(2); pp. 128-132 (2006).
Featherstone, J.D.B., Delivery Challenges for Fluoride, Chlorhexidine and Xylitol, BMC Oral Health; 6:S8, 5 pgs (2006).
Final Report: Study No. 1439, The Effect of Experimental Oral Care Products on Caries Formation in the Rat (similar to FDA #37), 18 pgs (2008).
Final Report: EFU-R-0701, Fluoride Uptake in Incipient Enamel Lesions After Dentifrice Treatment (FDA Test #40, 4 pgs (2007).
Food and Drug Administration, Anticaries Drug Products for Over-the-Counter Human Use: Final Monograph, Title 21, Federal Register, vol. 60, No. 194, Parts 310, 355, and 369, 2 pgs (1995).
Food and Drug Administration, US Dept of Health and Human Services; Guidance for Industry Q1A(R2) Stability Testing of New Drug Substances and Products, Rev. 2, 25 pgs (Nov. 2003).
Freitas, C., et al., Evaluation of the Substantivity of Chlorhexidine in Association with Sodium Fluoride in Vitro, Pesqui Odontol Bras, 17(1), pp. 78-81 (2003).
Garcia-Godoy F, et al, Maintaining the Integrity of the Enamel Surface: The Role of Dental Biofilm, Saliva, and Preventive Agents in Enamel Demineralization and Remineralization; Jour.Am.Dent. Assoc.,139; pp. 25S-34S (2008).
Goncalves R.H.P., et al., Species diversity of yeast in oral colonization of insulin-treated diabetes mellitus patients, Mycopathologia, 162, pp. 83-89 (2006).
Gonzalez-Gravina, et al., Oral candidiasis in children and adolescents with cancer, Identification of *Candida* spp, Medicina Oral, Patologia Oral y Cirugia Bucal, 12(6), pp. E419-423 (2007).
Grootveld, M., et al., Evidence for the Microbicidal Activity of a Chlorine Dioxide-Containing Oral Rinse Formulation in Vivo, J.Clin. Dentistry, vol. XII(3), pp. 67-70 (2001).
Gudlauggson, et al., Attributable mortality ofnosocomial candidemia, revisited, Clin. Infect. Dis. 37, pp. 1172-1177 (2003).
Gunsolley J.C., A Meta-Analysis of Six-Month Studies of Antiplaque and Antigingivitis Agents, Jour.Am.Dent. Assoc, 137; pp. 1649-1657 (2006).
Hajjeh, et al., Incidence of bloodstream infections due to *Candida* species and in vitro susceptibilities of isolates collected from 1998 to 2000 in a population-based active surveillance program, Journal of Clinical Microbiology, col. 42, No. 4, pp. 1519-1527 (2004).

Harakeh S, et al., Inactivation of Bacteria by Purogene, J.Appl. Bacteriol, 64(5), abstract (1 page) (1988).
Hazen S.L., et al., Human neutrophils employ the myeloperoxidase-hydrogen peroxide-chloride system to oxidize alpha-amino acids to a family of reactive aldehydes, Mechanistic studies identifying labile intermediates along the reaction pathway, J Biol Chem., 273(9), pp. 4997-5005 (Feb. 27, 1998).
International Conference on Harmonisation of Technical Requirements for Registration of Pharmaceuticals for Human Use (ICH), Guidance for Industry Q1A(R2) Stability Testing of New Drug Substances and Products, 24 pgs (2003).
Islam B, et al., Dental Caries: From Infection to Prevention, Med.Sci.Monit, 13(11): pp. RA196-RA203 (2007).
Jacobsen, et al., Mixed *Candida albicans* strain populatins in colonized and infected mucosal tissues, Federation of European Microbiological Societies Yeast Res 8, pp. 1334-1338, (2008).
Keyes, P.H., Dental Caries in the Molar Teeth of Rats: II. A Method for Diagnosing and Scoring Several Types ofLesions Simultaneously, Jour. of Dent. Res. 17(6), pp. 1088-1099 (1958).
Kidd E.A.M., et al. What Constitutes Dental Caries? Histopathology of Carious Enamel and Dentin Related to the Action of Cariogenic Biofilms, Jour. of Dent. Res., 83; pp. C35-C38 (2004).
Kirsch, Final Report—The evaluation of chlorine dioxide dentifrice formulations, University of Iowa, pp. 1-90, (2006).
Kleinberg et al., The pH of Dental Plaques in the Different Areas of the Mouth Before and After Meals and their Relationship to the pH and Rate of the Flow of Resting Saliva, Archives of Oral Biology, vol. 9, pp. 493-516, (1964).
Kolahi J, et al., Rinsing With Chlorhexidine Gluconate Solution After Brushing and Flossing Teeth: A Systematic Review of Effectiveness; Quintessence Int., 37(8), abstract (1 page) (2006).
Krishnaraju R.K., et al., Comparative Genomics and Structure Prediction of Dental Matrix Proteins, Advances inDental Res., 17; pp. 100-103 (2003).
Lendennman U, et al., Saliva and Dental Pellicle—A Review, Advances in Dental Res., 14; pp. 22-28 (2000).
Leone C.W., et al., Physical and Chemical Aspects of Saliva as Indicators of Risk for Dental Caries in Humans, Jour.Dent. Educ., vol. 65, No. 10, pp. 1054-1062 (2001).
Li L, et al., *Candida glabrata*, an emerging oral opportunistic pathogen, Journal of Dental Research, 86(3), pp. 204-215 (2007).
Lockhart S.R., et al. Natural defenses against Candida colonization breakdown in the oral cavities of the elderly, Journal of Dental Research, 78, pp. 857-868 (1999).
Luoma H, et al., A Simultaneous Reduction of Caries and Gingivitis in a Group of Schoolchildren ReceivingChlorhexidine-Fluoride Applications, Results After 2 Years; Caries Res., 12, 2 pages (1978).
Lynch, E, et al., Multicomponent Spectroscopic Investigations of Salivary Antioxidant Consumption by an Oral Rinse Preparation Containing the Stable Free Radical Species Chlorine Dioxide (CIO2); Free Radical Research, 26(3), pp. 209-234 (Mar. 1997).
Margolis H.C., et al., Role of Macromolecular Assembly of Enamel Matrix Proteins in Enamel Formation, Jour. ofDent. Res., 85, pp. 775-793 (2006).
Masschelein W.J., Chlorine Dioxide: Chemistry and Environmental Impact of Oxychlorine Compounds, AnnArbor Science Publishers Inc., Ann Arbor, Michigan, pp. 153-156 (1979).
Masschelein W.J., Chlorine Dioxide: Chemistry and Environmental Impact of Oxychlorine Compounds, AnnArbor Science Publishers Inc., Ann Arbor, Michigan, pp. 138-141 (1979).
McCarthy G.M., et al., Factors associated with increased frequency of HIV-related oral candidiasis, Journal of Oral Pathology and Medicine, 20, pp. 332-336 (1991).
Mjor, I.A., Dentin Permeability: The Basis for Understanding Pulp Reactions and Adhesive Technology, Braz. Dent. J., 20(1), pp. 3-16 (2009).
Mohammad A.R., et al., Clinical and microbiological efficacy of chlorine dioxide in the management of chronic atrophic candidiasis: an open studY, International Dental Journal, 54(3), pp. 154-158 (2004).
Moran G.P., et al., Antifungal Drug Susceptibilities of Oral *Candida dubliniensis* Isolates from Human Immunodeficiency Virus (HIV)-Infected and Non-HIV-Infected Subjects and Generation of Stable

(56) References Cited

OTHER PUBLICATIONS

Fluconazole-Resistant Derivative In Vitro., Antimicrobial Agents and Chemotherapy, 41(3), pp. 617-623 (1997).
Moran G.P., et al, Emergence of non-*Candida albicans Candida* species as pathogens, in R.A. Calderone (ed.), *Candida* and Candidaisis. Washington, DC: ASM Press, pp. 37-53 (2002).
Nguyen D.H., et al., Common Dental Infections in the Primary Care Setting, Am.Fam. Physician 77(6), pp. 797-802 (2008).
Ogaard, B, et al., Professional Topical Fluoride Applications—Clinical Efficacy and Mechanism of Action; Adv. Dent.Res. 8(2), pp. 190-201 (1994).
oxyfresh.com, "Flouride with Fresh Mint Mouthrinse," Oral Health Care, Oxyfresh Worldwide, Inc., http://web.archive.org/web/20061023030535/https://oxyfresh.com/dental/rinse_flouride.asp., 2 pages, (Oct. 23, 2006).
oxyfresh.com, "Flouride with Fresh Mint Mouthrinse," Oral Health Care, Oxyfresh Worldwide, Inc., http://web.archive.org/web/20080509170508/https://oxyfresh.com/dental/rinse_flouride.asp., 2 pages, (May 9, 2008).
oxyfresh.com, "Flouride Kit," Oral Health Care, Oxyfresh Worldwide, Inc., http://web.archive.org/web/20061023030354/https://oxyfresh.com/dental/ohkits_flouride . . . , 2 pages, (Oct. 23, 2007).
Pappas, et al., A Prospective Observational Study of Candidemia: Epidemiology, Therapy, and Influences on Mortality in Hospitalized Adult and Pediatric Patients, Clinical Infectious Diseases, 37, pp. 634-643 (2003).
Pashley D.H., Dynamics of the Pulpo-Dentin Complex; Critical Reviews in Oral Biology & Medicine, 7, pp. 104-133 (1996).
Pfaller, et al., Epidemiology of Invasive Candidiasis: a Persisitent Public Health Problem, Clinical Microbiolog Reviews, pp. 133-163 (Jan. 2007).
Redding, et al., *Candida glabrata* is an emerging cause of oropharyngeal candidiasis in patients receiving radiation or head and neck cancer, Oral Surgery Oral Medicine Oral Pathology Oral Radiology and Endodontics, 97, pp. 47-52 (2004).
Redding S.W., The role of yeasts other than *Candida albicans* in oropharyngeal candidiasis, Current Opinion in Infectious Diseases, 14, pp. 673-677 (2001).
Rees, et al., The Epidemiological Features of Invasive Mycotic Infections in the San Francisco Bay Area, 1992-1993: Results of Population-Based Laboratory Active Surveillance, Clinical Infectious Diseases, 27, pp. 1138-1147 (1998).
Rex, et al., Development of interpretive breakpoints for antifungal susceptibility testing: conceptual framework and analysis of in vitro—in vivo correlation data for fluconazole,itraconazole, and *Candida* infections, Subcommittee on Antifungal Susceptibility Testing of the National Committee for Clinical Laboratory Standards. Clinical Infectious Diseases,24(2), pp. 235-247 (Feb. 1997).
Rex J.H., et al. Practice guidelines for the treatment of candidiasis, Clinical Infectious Diseases, 30 (4), pp. 662-278 (2000).
Robinson C, et al., The Chemistry of Enamel Caries; Critical Reviews in Oral Biology & Medicine, 11 (4), pp. 481-495 (2000).
Roller S.D., et al., Mode of Bacterial Inactivation by Chlorine Dioxide, Water Research, 14, pp. 635-641 (1980).
Rose L.F., et al., Periodontics: Medicine, Surgery, and Implants, St. Louis: Mosby, Inc., pp. 20, 70, 847-848 and 854, (2004).
Samaranayake L.P., et al., Oral candidiasis and human immunodeficiency virus infection, Journal of Oral Pathology and Medicine, 18, pp. 554-564 (1989).
Samonis G, et al., Oropharyngeal candidiasis as a marker for esophageal candidiasis in patients with cancer, Clinical Infection Diseases, 27, pp. 283-286 (1998).
San-Blas et al., Fungal morphogensis and virulence, Medical Mycology, 38, pp. 79-86 (2000).
Sharma G, et al., Oral manifestations in HIV/AIDS infected patients from India, Oral Diseases, 12, pp. 537-542 (2006).

Shinada, et al., A randomized double blind crossover placebo-controlled clinical trial to assess the effects of a mouthwash containing chlorine dioxide on oral malodor, Trials, BioMed Central, London GB, vol. 9, No. 1, 8 pgs (Dec. 9, 2008).
Silwood C.J.L., et al., A multifactorial investigation of the ability of oral health care products (OHCPs) to alleviate oral malodour, Journal of Clinical Periodontology, 28, pp. 634-641 (2001).
Slavinsky J, et al., Th1/Th2 cytokine profiles in saliva of HIV-positive smokers with oropharyngeal candidiasis, Oral Microbiology and Immunology, 17, pp. 38-43 (2002).
Soysa N.S., et al., The impact of cigarette/tobacco smoking on oral candidiasis: an overview, Oral Diseases, 11, pp. 268-273 (2005).
Spellberg, et al., Current Treatment Strategies for Disseminated Candidiasis, Clinical Infection Diseases, 42, pp. 244-251 (2006).
Stookey G.K., et al., Animal Caries Models for Evaluating Fluoride Dentifrices; Advances in Dental Res. 9(3);pp. 198-207 (1995).
Takasawa H, et al., An elderly case of Type 2 diabetes which developed in association with oral and esophageal candidiasis, Internal Medicine, 46(7), pp. 387-390 (2007).
Taylor G.W., et al., Special Review in Periodontal Medicine: Periodontal disease: associations with diabetes, glycemic control and complications, Oral Diseases 14, pp. 191-203 (2008).
The Proprietary Association Subgroup on Fluoride Dentifrices, Standards for FluorideDentifrices, 4 pgs (Mar. 11, 1978).
Thompson et al., Coevolution of Morphology and Virulence in *Candida* Species, Eukaryotic Cell, Vo. 10, No. 9, pp. 117-1182 (2011).
United States Environmental Protection Agency, Alternative Disinfectants and Oxidants Guidance Manual, 2 pgs (1999).
Vargas, K. et al., Carriage frequency, intensity of carriage, and strains of oral yeast species vary in the progression to oral candidiasis in human immunodeficiency virus-positive individuals, Journal of Clinical Microbiology 40(2), pp. 341-350, (2002).
Vazquez, J., Diagnosing and Managing Oropharyngeal candidiasis, Infections in Medicine 24, pp. 427-436, (2007).
Viale, P., Candida Colonization and Candiduria in Critically Ill Patients in the Intensive Care Unit, Drugs Suppl 1, 51-57, abstract (1 page) (2009).
Villhauer A, et al., Bactericidal Activity of Stabilized Chlorine Dioxide Against Polymicrobial Biofilms; International Assoc. for Dental Research Poster #3417, General Session, Apr. 1-4, 1 page (2009).
Wang L, et al., Mimicking the Self-Organized Microstructure of Tooth Enamel; J. Phys. Chem C Nanometer Interfaces112(15), 16 pgs (2008).
Warrick J.M., et al., Caries-Preventive Effects of Sodium and Amine Fluoride Dentifrices, Am. J.Dent, 12(1), pp. 9-13 (1999).
Wei, M.K, et al., Plasma membrane damage to Candida albicans caused by chlorine dioxide (ClO2), Letters in Applied Microbiology 47(2), pp. 67-73, (2008).
Whelton H., et al., The Use of Combinations of Caries Preventive Procedures; Jour. Dent. Educ., vol. 65, No. 10, pp. 1110-1113 (2001).
Whitten, Kenneth W, et al., General Chemistry (6th Ed) Fort Worth, TX, Saunders College Publishing/Hartcourt college Publishets, ISBN 978-0-03-072373-5, pp. 27-46 (2000).
Williams, et al., Isolation and identification of Candida from the oral cavity, Oral Disease, 6(1), 3-11 (Jan. 2000).
Willis A.M., et al., Oral candidal carriage and infection in insulin-treated diabetic patients, Diabetic Medicine, 16, pp. 675-679 (1999).
Wirthlin M.R., et al., Chlorine dioxide and water rinses in gingivitis, Rowpar Pharmaceuticals Study Report, OSAP Annual Symposium, 1 page, (2003).
Wirthlin M.R., et al., Formation and Decontamination of Biofilms in Dental Unit Waterlines; J. Periodontal, 74 (11), pp. 1595-1609 (2001).

* cited by examiner

METHOD AND COMPOSITION FOR PREVENTION AND TREATMENT OF ORAL FUNGAL INFECTIONS

CROSS REFERENCE TO RELATED APPLICATIONS

This application claims priority to: U.S. application Ser. No. 12/500,163 filed on Jul. 9, 2009 entitled "METHOD AND COMPOSITION FOR PREVENTION AND TREATMENT OF ORAL FUNGAL INFECTIONS", which claims priority to U.S. Provisional Application No. 61/079,532 entitled "METHOD AND COMPOSITION FOR PREVENTION AND TREATMENT OF ORAL FUNGAL INFECTIONS" filed on Jul. 10, 2008, the disclosures of which are incorporated herein by reference.

BACKGROUND OF THE INVENTION

1. Field of Invention

The present invention relates to the use of stabilized chlorine dioxide in topical oral compositions to prevent oral fungal infections.

2. Description of Related art

Thrush, clinically termed oral candidiasis, is the most common opportunistic fungal infection in humans. Thrush is caused by the imbalance of microorganisms in the oral cavity allowing *Candida* species (fungus or yeast) to grow out of control causing infection with development of white lesions and potentially spreading to other parts of the body, including the esophagus, lungs, liver, and skin. Four types of oral thrush are recognized: angular cheilitis, denture stomatitis, erythematous candidiasis, and pseudomembranous candidiasis. Thrush may involve several species of *Candida* resident in the oral ecology, each with its own characteristics and susceptibility to treatments.

*Candida* species are found in the oral cavity as normal commensal microorganisms and may overgrow when the host response is weakened, such as in immunocompromised individuals. Immunocompromised conditions include HIV/AIDS, nutritional deficiencies, metabolic disorders such as diabetes, malignancies, xerostomia, medication side effects, aging, pregnancy, Sjogrens syndrome, dentures, and smokers.

The amount of *Candida* colonization in the oral cavity of denture wearers was higher (Abu-Elteen and Abu-Alteen, 1998). Studies that observed oral cavities of immunocompromised patients indicate that patients who wore dentures were associated with increased numbers of yeasts, more specifically *Candida* species (Willis et al., 1999; Gonclaves et al., 2006).

The oral microbiological environment can be significantly affected by tobacco smoking, specifically having an effect on oral bacteria and fungi, particularly *Candida*. The impact of smoking on thrush varies in combination to pre-existing conditions (dentures, HIV, and diabetes) (Soysa and Ellepola, 2005). Increasingly, studies show smokers have greater numbers of oral *Candida* carriage than non-smokers (Abu-Elteen and Abu-Alteen, 1998; Willis et al., 1999). Several studies suggest that smoking has a significant affect on the incidence of thrush in immunocompromised patients. Smoking is an important risk indicator for thrush, especially in HIV infected patients (Chattopadhyay et al., 2005). Conley et al. (1996), Campisis et al. (2002), and Slavinsky et al. (2002) found significant associations between thrush and smoking in HIV infected individuals. Willis et al. (1999) reported that seventy seven percent (77%) of diabetic patients carried *Candida* species in the mouth. Among these patients, there was a significant increase in the tobacco smokers. Smoking alone or in combination with other factors may be contributory to the development of thrush.

Thrush is the most common and earliest oral manifestation of HIV/AIDS caused mostly by *Candida* species. HIV/AIDS patients commonly have dry mouth, pain and may develop oral lesions from thrush, which can interfere with oral intake of food and lead to severe malnutrition. HIV related oral manifestations occur in an estimated 30-80% of HIV patients and are often under diagnosed and misdiagnosed. Thrush will develop in up to 90% of all advanced untreated HIV infections, with 60% experiencing at least one episode per year with recurrences. (Samaranayake et al., 1989; McCarthy et al., 1991). Thrush is often the first indicator of progression from HIV to AIDS; this was confirmed in a study by Sharma et al. (2006) who showed that there was a 2.5 time increased risk of progression from HIV to AIDS in patients with thrush. The progression indicates the immunological decline and is manifest by decreased $CD4^+$ T-lymphocyte cell counts, which contribute to the risk of developing both thrush and oral hairy leukoplakia. Chattopadhyay et al. (2005 and 2007) reported a correlation that showed low $CD4^+$ counts and smoking are independent risk factors for thrush and oral hairy leukoplakia.

Cancer treatments, cytoxic chemotherapy and radiotherapy, have short and long term side effects including thrush. The incidence of thrush in cancer patients ranges widely depending on the stage of the cancer, doses of treatments, method of diagnosis and other predisposing factors. Davies et al. (2006) found that 66% of cancer patients carried oral *Candida* and other yeast species and 30% had thrush. Another study reported 25% of patients receiving radiation for head and neck cancer had high prevalence of *Candida* colonization in the oral cavity (Redding et al., 2004). There is evidence that thrush can also spread to the esophagus and develop esophageal candidiasis (Samonis et al., 1998). This finding underscores the importance of preventing and reducing the risk of thrush in all immunocompromised patients.

Diabetes mellitus patients have increased susceptibility to certain infections, which can lead to poor metabolic control. Studies have shown that oral candidal infections are more common in diabetic patients than in non-diabetics. Takasawa, et al. (2006) reported a case study of the association of diabetes with thrush. The case involved a 75-year old healthy patient who developed diabetes and candidiasis (oral and esophageal) within a short interval with limited risk factors. The patient was diagnosed with type 2 diabetes accompanied by severe thrush and esophageal candidiasis. The case indicates a relationship between diabetes and oral infection, wherein diabetes may cause oral infections and conversely oral infection may stimulate the development of diabetes (Taylor, 2008).

*Candida* species have been isolated from oral cavities of diabetic patients. Willis et al., 1999 found 77% of diabetic patients carried oral *Candida* species. This study also established that a number of contributory factors affect candidal colonization; these include smoking, dentures, type and duration of diabetes and the degree of glycaemic control. Willis et al. also isolated several different species of *Candida* in combination to the predominate species, *Candida albicans*. Goncalves et al. (2006) investigated the oral yeast colonization and antifungal susceptibility in diabetic patients, isolating several non-albican species, including *C. tropicalis, C. glabrata, C. krusei, C. rugosa, C. guillermondii,* and *C. parapsilosis*. This study tested the resistance of these species to the antifungal treatment fluconazole, and found high levels of resistance by the non-albican species.

Treatment and therapy of thrush varies with each medical condition. Prevalent recommended therapies currently include nystatin, azole antifungal agents and amphotericin B preparations. Initial episodes of oral thrush in healthy children and adults can be treated effectively with topical therapies, including clotrimazole troches, nystatin suspensions or pastilles (Rex et al., 2000); however, individuals with immunocompromised systems will often have recurrent episodes of infections making it difficult to treat with these therapies. A resistance to the therapies may also develop with any regimen. Most patients will initially respond to topical therapies; however, immunocompromised patients will often experience symptomatic relapses sooner.

Oral azoles, nystatin, amphotericin B, and chlorhexidine are several therapies administered orally for the treatment of oral thrush. The azoles include fluconazole, itraconazole, and ketoconazole, which can be capsules/tablets or liquid suspensions taken by mouth and absorbed by the gastrointestinal tract. Oral fluconazole is better tolerated than itraconazole and ketoconazole. Capsule azoles are found to be less effective than the oral suspensions due to variable absorption. Nystatin and amphotericin B are less effective at preventing fungal infections than prophylactic therapies with fluconazole. Most recurring infections are due to prior use of the therapies where the fungi developed resistance to the treatments; individuals with recurring infections must change from one oral treatment to other treatments over time. For instance, thrush infections resistant to fluconazole will respond to oral itraconazole about two-thirds of the time. When the patient is not responding to itraconazole, amphotericin B oral suspension may be effective. A high dose of medication for a short period is recommended to reduce the development of candidal resistance.

Chlorhexidine gluconate (CHX) has antifungal properties, and it is widely used by dental professionals as an antimicrobial oral rinse. While it may be effectively used as a preventive to the development of thrush, it has not been proven effective as a treatment. Objectional taste and teeth staining lead to problematic use of CHX continuously. Worthington et al. (2008) reviewed literature pertaining to the effectiveness of interventions and medications for treating thrush in cancer patients, concluding that drugs absorbed or partially absorbed from the GI tract are more effective than those not absorbed (including nystatin and amphotericin B).

*Candida albicans* is usually the predominant species in thrush, however other species of *Candida* have been emerging as significant pathogens in patients. Non-albicans species of *Candida* have been isolated in combination with *C. albicans* in cancer and HIV patients. They have been observed to cause more severe immunosuppression, and consequently are more difficult to treat. Cartledge et al. (1999) reported that from 100 non-albicans isolates obtained from HIV patients with thrush, 88 were resistant to fluconazole. There is a need for a treatment with high susceptibility to all types *Candida* species.

Non-albicans species commonly found in saliva of patients with oral lesions (with or without oral thrush) include *C. tropicalis, C. glabrata, C. parapsilosis, C. Krusei*, and *C. dubliniensis* (Oliveria et al., 2007; Coleman et al., 1997). A study by Davies et al. showed 25% of samples taken involved non-albicans species (including *C. glabrata, C. dubliniensis*, and *C. tropicalis*) were the predominant organisms and a contributing factor in 19% of samples taken from cancer patients with thrush (2006).

*Candida glabrata*, formerly known as *Torulopsis glabrata*, is a significant human pathogen and is the second leading cause of oral thrush (Li et al., 2007). Its association with thrush is unclear as some research suggests that it is only a commensal organism and does not contribute directly to infections. However, it is also observed that its presence with *C. albicans* in HIV-positive patients present more severe and difficult to treat forms of thrush, requiring higher doses of fluconazole medication. Other treatments for *C. glabrata* infections include itraconazole and amphotericin B solutions; however much like other treatments for fungal infections, a percentage of *C. glabrata* treated with these medications become resistant to them. *C. glabrata* is dose-dependent to fluconazole, and may require higher doses than does *Candida albicans* in order to be effective. The *C. glabrata* is the second most frequent species in elderly patients with and without dentures. Lockhart et al. found that patients with dentures had an increase in *C. glabrata* frequency from 36% to 58% in elderly ages 70-79 yrs and 80 years and older, respectively (1999). *Candida glabrata* is an increasingly common species found in all cases of thrush infections and is very difficult to treat due to its resistance to commonly used drugs.

*Candida dubliniensis* has been found mostly in oral cavities of HIV-positive and AIDS patients, especially those that received fluconazole therapy. *C. dubliniensis* has phenotypic characteristics similar to *C. albicans* and displays the same antifungal susceptibilities. Research has found that fluconazole can be ineffective for managing diverse infections that include *C. albicans* and *C. dubliniensis* species due to their combined development of resistance to the drug (Moran et al., 1997). HIV-positive patients with large doses of medications are more vulnerable to developing resistance. *C. dubliniensis* has been effectively treated with several common azoles therapies including ketoconazole, itraconazole, and amphotericin B. *C. dubliniensis* is also susceptible to triazoles, including voriconazole, posaconazole and ravuconazole.

*Candida krusei* colonization in the oral cavity is increasingly common. Thrush with *C. krusei* also includes the presence of *C. albicans*. Itraconazole solutions were proven effective in treating *Candida krusei* in thrush patients, but *C. krusei* infections were resistant to both fluconazole and ketoconazole (Cartledge et al., 1999).

Thrush caused by the colonization of *Candida tropicalis* is rare and is susceptible to any antifungal treatment. However, its presence in thrush of cancer patients receiving chemotherapy can be very pathogenic and may lead to hemotologic infections.

New orally administered, ingested antifungal drugs, including terbafine, azoles, and echnocandins, are currently being tested as treatments of thrush. Studies show these new drugs may be more effective in treating thrush involving non-albicans infections. For instance, Bagg et al. (2005) shows in vitro tests of voriconazole to be effective on fungal oral infections which are resistant to other antifungals including fluconazole and itraconazole. However, this study also showed *C. glabrata* not to be fully susceptible to voriconazole. Voriconazole must be administered with care due to its significant drug interactions and its contraindication with several other drugs.

There is a limited capacity of current pharmaceutical drugs to prevent and treat *Candida* infections. *Candida* species are recognized to become resistant to most fungicidal treatments over time, and different species are more or less resistant to treatment and various medications. In several cases, the resistance to antifungals can be reduced with use at higher doses but such dosing only can be used for a short time (Rose, 2004). Certain individuals suffering from oral thrush (cancer, HIV, and diabetes) require extended treatments that correspond to their medical conditions. Similarly, pregnant women and the elderly may require oral thrush treatments extending over several months and therefore may not be able to use the higher dosages over extended time without untoward consequences. Immunocompromised patients often are diagnosed with underlying conditions that require several medications, complicating treatment with the prospect of negative drug interactions. Given the limitations of antifungals' effectiveness against candidal infections, the higher doses may be useful and appropriate largely for mild cases because most severe cases require longer periods of treatment.

The treatment of thrush becomes particularly difficult when several different *Candida* species are present and when other existing systemic conditions complicate treatment. Prevention of thrush among populations most at risk is preferable than treatment because it permits immunocompromised patients to maintain their health and diet and may lead to less severe and/or less frequent cases. Therefore, there is a need for a composition for both the prevention and the treatment of thrush, which is safe and effective in inhibiting, reducing and eliminating all oral *Candida* species involved in infections.

SUMMARY OF THE INVENTION

The present invention relates to a composition containing stabilized chlorine dioxide that may be used for treatment of the mouth either in a solution, for example as a mouthwash, in concentrations below approximately 0.8% (w/v) for the control of disease-causing bacteria, bacterial plaque, and oral malodor. Mint oils or extracts may be added to flavor an oral rinse or oral spray of stabilized chlorine dioxide in such a manner that the flavoring would not interact with stabilized chlorine dioxide or affect the stability of the formulation.

It is therefore a primary object of the present invention to provide a composition of stabilized chlorine dioxide to prevent and treat specific *Candida* species, including *C. dubliniensis, C. glabrata, C. krusei,* and *C. tropicalis.*

Another object of the present invention is to provide a composition of stabilized chlorine dioxide in a concentration equal to or greater than 0.4% (w/v) to prevent and treat fungal infection in the oral cavity.

Still another object of the present invention is to provide a method for prevention and treating fungal infection in the oral cavity.

Yet another object of the present invention is to provide a method for inhibiting the growth of *Candida albicans, C. dubliniensis, C. glabrat* and *C. krusei.*

DETAILED DESCRIPTION OF THE PREFERRED EMBODIMENT

The term chlorine dioxide is widely used in the industry. Those skilled in the art will and do appreciate the various forms or variations thereof, which are available to perform certain intended functions and purposes. Furthermore, U.S. Pat. No. 3,271,242 describes a form of stabilized chlorine dioxide and a method of making the product and a mechanism of action, which is particularly useful in carrying out the present invention.

Masschelein (1979) teaches that the bactericidal properties of chlorine dioxide were well known before its first applicable use in the 1950's. Today, chlorine dioxide is used as a drinking water treatment obtained from sodium chlorite producing a solution free of chlorine. Stabilized chlorine dioxide is an aqueous solution comprising chlorite and stabilizers. When the pH of stabilized chlorine dioxide lowers from a neutral pH, molecular chlorine dioxide releases from the aqueous solution. This mechanism of action of stabilized chlorine dioxide has bactericidal and bacteriostatic effects on the microbial ecology of aerobic, facultative, and anaerobic pathogenic bacteria.

Previous inventions contemplate the use of stabilized chlorine dioxide for the prevention and treatment of gingivitis and periodontitis, as well as dental caries (Ratcliff, U.S. Pat. Nos. 5,200,171 and 5,348,734). Theses patents describe the basic composition and use of stabilized chlorine dioxide oral rinse of the present invention. The Ratcliff inventions claim the prevention and treatment of dental diseases by reducing the number of oral microbial pathogens, including yeasts such as *Candida albicans*, at concentration ranges between about 0.005-0.5% stabilized chlorine dioxide. This prior art does not contemplate the use of stabilized chlorine dioxide for the prevention of oral thrush or in the inhibition of growth of other *Candida* species.

Prior art compositions that have been used and tested have been accepted to an extent of efficacy in treatments and prevention of abnormal conditions of the epithelium bodily orifices, such as oral nasal, ocular, auditory, rectal, vaginal, and urethral canal orifices (Ratcliff, U.S. Pat. Nos. 5,489,435 and 5,618,550). The claims of the previous invention described the in vitro study of *Candida* culture exposed to a stabilized chlorine dioxide solution resulting in more than 99% of *Candida albicans* reduced within 10 seconds.

Several antifungal compounds claim to treat fungal infections of the oral cavity (Francois U.S. Pat. No. 5,707,975 and Lipton U.S. Pat. No. 6,780,838). Francois et al. present an antifungal invention comprising of a cyclodextrin formulation for oral administration to treat fungal infections. Lipton et al. claim an invention with a therapeutically effective amount of one or more selected peptides in combination with a fungicide as a treatment of oral fungal pathologies. However, these inventions do not propose use of stabilized chlorine dioxide as the active ingredient for prevention and treatment of thrush.

There are several well-established advantages to stabilized chlorine dioxide as an antifungal including its broad range of antiseptic abilities, established safety, method of action, ability to be used over time, its low cost (relative to the aforementioned antifungal drugs), and ease of use (Mohammed et al., 2004). The present invention consists of stabilized chlorine dioxide at concentration ranges that exhibit fungistatic and fungicidal properties and may be used for the prevention and treatment of fungal infections and diseases in the oral cavity. Unlike, current treatment for oral fungal infections, the present invention can be used for any length of time without decreasing effectiveness due to fungal resistance, is effective against several major species of *Candida* found to cause oral thrush, does not have objectional taste, and does not cause teeth staining.

For liquids such as mouthwash, the standard unit of measurement when expressing concentration is weight-volume percentage. That is, a certain weight of component, solid, liquid, or dissolved in a solvent, is present in a certain volume of total mouthwash. For example, preferred concentrations of stabilized chlorine dioxide as used herein may be in the range of 0.0004% to 2% (w/v).

The terms "topical oral care composition" and "oral composition" as used herein are meant to describe a product, which is not intentionally swallowed for purposes of systemic administration of therapeutic agents, but is retained in the oral cavity for a sufficient time to contact substantially all of the dental surfaces and/or oral mucosal tissues for purposes of oral activity.

The present invention focuses on fungicidal properties of stabilized chlorine dioxide. Present evidence shows that the effects of stabilized chlorine dioxide on several *Candida* species significantly reduce candidal reproduction, both individual species and species in colonial forms. There is no prior art claiming stabilized chlorine dioxide as a preventative or treatment on specific *Candida* species, including *C. dubliniensis, C. glabrata, C. krusei,* and *C. tropicalis*.

Supporting evidence for the antifungal properties of the present invention are observed in Mohammad et al.'s clinical study of investigating the efficacy of chlorine dioxide mouth rinse as a topical antiseptic treating chronic atrophic candidiasis (2004). The study concluded that a 0.8% concentration chlorine dioxide mouth rinse demonstrated management of chronic atrophic candidiasis. Results indicated significant clinical improvement after 10 days. Mohammad et al. shows that the 0.8% chlorine dioxide had a statistically significant effect on improving the oral soft tissues of the thrush as well as reducing the microbial count. The present invention and this study indicate thrush generally, and overgrowth of certain species of *Candida* specifically, can be prevented safely and effectively with dosages lower than those employed by Mohammad et al.

Wirthlin et al. (2001) supports the present invention's safety and effectiveness of 0.1% stabilized chlorine dioxide oral rinse. Thirty-eight subjects in the clinical study tested 0.1% oral rinse and a placebo for 6 months. Wirthlin et al. observed no clinical overgrowth of *Candida* species or reported no adverse effects on teeth, restorations, or soft tissues with the use of the oral rinse. Additionally, the oral rinse did not affect taste or stain the teeth of the patients. It was also determined from the study that yeasts, enterics, black-pigmented *Porphyromonas, Prevotella, Actinomyces, Fusobacteria* or *Streptococci* species showed no resistance or decreased susceptibility to stabilized chlorine dioxide.

The present invention concerns oral care compositions including oral washes or rinses, oral gels, toothpaste dentifrices, and oral spray in a solution comprising of stabilized chlorine dioxide. It contemplates the use of stabilized chlorine dioxide as a fungistatic and fungicidal agent against yeast species involved in oral disease such as, but not limited to *C. albicans, C. glabrata, C. krusei,* and *C. dubliniensis*. The mechanism for the composition includes the determined inhibitory and fungistatic activity of the stabilized chlorine dioxide compositions against four clinical isolates of *Candida*.

The present invention consists of a stabilized chlorine dioxide composition, which acts as a fungistatic agent on the aforementioned *Candida* species at a concentration ranges between 0.0004%-0.05% (w/v) and as a fungicidal agent on the aforementioned *Candida* species at a concentration ranges between 0.4%-0.8% (w/v).

The present invention proclaims the use of stabilized chlorine dioxide oral rinse, dentifrice, oral spray, or oral gel as a fungistatic treatment on *Candida* species with a minimum concentration of 0.0004% (w/v). The present invention contemplates the ability of stabilized chlorine dioxide as a fungistatic agent against *Candida* species involved in thrush. For example, it was shown in the present invention that the re-growth of *C. albicans, C. dubliniensis, C. glabrata,* and *C. krusei* were inhibited, showing a fungistatic effect on fungi involved in thrush. There is little or no prior research claiming inhibited growth of *Candida* species, including *C. albicans, C. dubliniensis, C. glabrata,* and *C. krusei*, after exposure to stabilized chlorine dioxide. Present research indicates a stabilized chlorine dioxide composition has fungistatic effects on the *Candida* species ultimately leading to fungal cell death. This inhibition of cellular metabolism and cell function effectively inhibits or controls the overgrowth and formation candidal infections, the main contributors to human fungal infections.

The present invention has an effect of killing and reducing the number of *Candida* fungi at concentrations lower than that known in the prior art. The present invention established the fungicidal kinetics of the antimicrobial characteristics of stabilized chlorine dioxide against *Candida* species at minimum fungicidal concentrations of equal to or greater than 0.4% (w/v). The present invention acts as a fungicide on the following fungi: *C. albicans, C. dubliniensis, C. glabrata,* and *C. krusei*. Given the predominance of these *Candida* species, individually and in naturally occurring colonies, a stabilized chlorine dioxide oral composition is believed to be effective on the majority candidal fungi involved in the oral fungal infection (thrush).

The specific mechanism in which chlorine dioxide inactivates fungi and bacteria is currently postulated and researched. Therefore, it is believed that the present invention's fungistatic properties are due to inhibition of protein synthesis and/or to the inability of the cell to maintain membrane permeability and inhibited metabolic processes. Due to these effects on fungi and bacteria, a stabilized chlorine dioxide oral composition can inhibit plaque production and progression to oral diseases and thrush. This can be accomplished by individuals rinsing their mouths with said composition in a concentration range of 0.0004% to 0.8% (w/v) or brushing teeth and thereby exposing the oral cavity to the active ingredients in comparable concentration, or by using an oral spray in the oral cavity, or by other comparable delivery mechanism. The following mechanisms of action specify the explanations for fungicidal and bacterial kill by chlorine dioxide.

The specific mechanism of action of chlorine dioxide on cells has been debated for a number of years. Early research showed that chlorine dioxide's primary effect was the disruption of protein synthesis, leading to cell death (Benarde et al., 1967). Results from Benarde's studies clearly showed an abrupt inhibition on protein synthesis. Explanations for this occurrence on the cells included possible inhibition of amino acid activation, inactivation of messenger RNA (which prevents translation), and destruction of ribosomes by chlorine dioxide (which causes a loss in cell contents by leakage).

A later study, however, provided an alternate hypothesis to the precise mechanism of action of chlorine dioxide on cells. Roller et al. studied the effects of chlorine dioxide on dehydrogenase enzymes, protein synthesis, and deoxyribonucleic acid of bacteria (Roller et al., 1986). This study found that total dehydrogenase enzymes were inhibited completely within the first 5 seconds of reaction by chlorine dioxide and protein synthesis was partially inhibited. The dosage of chlorine dioxide used was found to be proportional to the extent of inhibition. These studies concluded that the primary effect of chlorine dioxide on cells was occurring in an area in the cell other than the dehydrogenase enzymes, protein-synthesizing complex, or DNA. It was determined that inhibition of protein synthesis of cells, indeed, contributed to cell death. However, Roller et al. concluded that an impairment of the cell's functions is occurring even before protein synthesis. Chlorine dioxide did not cause cell inactivation by altering or impairing the cell's DNA. An explanation or theory of the cell deaths by chlorine dioxide in this study is by a reaction with or oxidation of components related to enzyme activity of the cell (Roller et al., 1986).

Berg et al. (1986) studied the effect of chlorine dioxide on membrane functions of *Escherichia coli*, finding that the permeability control was impaired, leading to cell death. This study also showed that the inactivation by the chlorine dioxide did not cause a significant loss of intracellular macromolecules existing inside the cell to the surroundings. However, the membrane damage led to the loss of intracellular potassium destroying the trans-membrane ionic gradient; this is understood in the research to result in lethal inhibition of the metabolic processes and cell death. Thus, the permeability barrier of the cell was determined to be important to the sensitivity to chlorine dioxide and growth characteristics of the cell (Berg et al., 1986).

The present research evidence suggests that stabilized chlorine dioxide causes fungistatic and fungicidal effects, as well as bactericidal and bacteriostatic effects, on the fungal and bacterial cells, which ultimately lead to cell death. The current knowledge relative to the mechanism of action of chlorine dioxide on cell morphology indicates that *Candida* species would not be able to develop resistance to the method of action.

In Vitro Evaluation of Stabilized Chlorine Dioxide Oral Rinse Containing Stabilized Chlorine Dioxide Susceptibility of *Candida* Species:

To test the fungistatic and antifungal properties of stabilized chlorine dioxide oral rinse against several *Candida* species, as measured by minimum inhibitory concentration (MIC), minimum fungicidal concentrations (MFC), and time-kill colony counts after exposure, the following experiments were performed.

Materials

Four clinical isolates of *Candida*, including one each of *C. albicans, C. glabrata, C. krusei,* and *C. dubliniensis*

Stabilized chlorine dioxide oral rinse (0.8% concentration)

Chlorhexidine gluconate (20% stock solution)

RPMI 1640: Buffered with MOPS [3-(N-morpholino) propanesulfonic acid], with glutamine, without bicarbonate, pH=7.0. Prepared according to manufacturer's specifications and filter sterilize.

Potato Dextrose Agar: Potato dextrose agar 39 g, Agar 1 g, Distilled water 1 L

Cereal (oatmeal) Agar: Heinz baby oatmeal cerial 100 g, Agar 15 g, Distilled water 1 L Yeast Nitrogen Base: Yeast Nitrogen Base 6.7 g, Dextrose 5 g, Distilled water 1 L, Filter sterilize (All media stored at 2-8° C.)

Supplies

Adjustable volume pipettes, bunsen burner, cell counter, disposable serological pipettes, eppendorf repipettor, hemacytometer, 35° C. incubator, inoculation loop, microscope, microtiter plates, multichannel pipettor, pipette tips, sterile conical tubes (15 ml), sterile saline (0.85%), sterile water, sterile cotton swab, vortex mixer, weighing scale.

Experimental Methodology—Susceptibility Testing

Serial dilutions of the stabilized chlorine dioxide oral rinse were combined with inoculum (0.5-2.5×10$^3$ colony forming units (CFU/mL)) in 96-well microdilution trays and incubated at 35° C. for 24 hours.

Solutions of specified concentrations (concentration range up to 0.8% (w/v)) in the minimum inhibitory concentration (MIC) were tested according to the standard method described in NCCLS M27-A document. The plates were removed from incubation after 24 hours. The MIC was recorded as the lowest concentration to inhibit 50% of fungal growth as compared to the growth control (no drug exposure).

Minimum fungicidal concentration (MFC) testing was determined according to modifications suggested by Canton et al. (2003). Contents of each clear well from the MIC assay were sub-cultured onto potato dextrose agar. In order to avoid antifungal carryover, the aliquots were allowed to soak into the agar and were streaked for isolation once dry, removing the cells from the drug source. The MFC was measured as the lowest concentration at which ≥99.9% of *Candida* cells were reduced from the starting inoculum count.

The time-kill assay was performed by adding inocula (0.5-2.5×10$^3$ CFU/mL) of *Candida albicans, C. dubliniensis, C. glabrata,* and *C. krusei* to serial dilutions of concentrations ranging from 0.1-0.8% of stabilized chlorine dioxide oral rinse for 30 second and 1-minute exposure times. Following exposure, 100 µl aliquots were diluted 50% with 0.85% saline and plated onto potato dextrose agar plates. The aliquots were allowed to dry and then were streaked to remove the yeast from the compound. The plates were incubated at 35° C. for 24 hours. Colony counts were taken and were compared to initial inoculum. The same test was done treating the four *Candida* species with chlorhexidine gluconate at concentrations ranging from 0.015-0.12%. Chlorhexidine gluconate at concentration 0.12% is commonly prescribed to patients with oral disease.

All tests were performed in duplicate.

Results and Conclusions

The stabilized chlorine dioxide oral rinse showed strong inhibition against all strains of *Candida* species tested. The MIC range was 0.0004-0.05% (w/v) concentration (Table 1). The concentration at which *C. albicans* and *C. dubliniensis* were inhibited by stabilized chlorine dioxide oral rinse was 0.05%. *C. krusei* and *C. glabrata* both have lower concentrations of 0.025% and 0.0004%, respectively. The MFC range for all species was found to be greater than or equal to 0.4% concentration (Table 2).

Time-kill at 30 seconds and 1-minute exposures were also determined from this study. It has been determined that stabilized chlorine dioxide oral rinse is very effective in killing *Candida* species completely within 30 seconds of exposure at a concentration of 0.8% stabilized chlorine dioxide (Table 3). A 0.4% concentration solution also showed reduction of the count of *Candida albicans* after 30 seconds as shown in Replicate 1 and Replicate 2. This suggests that stabilized chlorine dioxide oral rinses at higher concentrations have a fungicidal effect within 1 minute of exposure at concentrations between 0.4% and 0.8%. Chlorhexidine gluconate is commonly prescribed at a concentration of 0.12% for the treatment of oral diseases and was used as a positive control. The chlorhexidine gluconate concentrations tested did not reduce the colony count of any of the *Candida* species within one minute of exposure (Table 4).

The in vitro test results of stabilized chlorine dioxide against *Candida* species shows fungistatic and fungicidal properties at the suggested concentrations. The present invention relates to use of stabilized chlorine dioxide as a pharmaceutically acceptable topical oral care product, including washes, rinses, soaks, pastes, gels, and aerosol sprays. The compositions of the present invention may be used to prevent or treat fungal infections and diseases, such as candidiasis or thrush. The present invention may also be used as a substitute or adjunct therapy to current treatments for oral fungal infections to promote overall oral health, especially for immunocompromised individuals.

TABLE 1

Minimum inhibitory concentrations (MIC) of stabilized chlorine dioxide rinse.

| Candida Species | MIC of stabilized chlorine dioxide rinse |
|---|---|
| C. albicans | 0.05% |
| C. dubliniensis | 0.05% |
| C. glabrata | 0.0004% |
| C. krusei | 0.025% |

TABLE 2

Minimum fungicidal concentrations (MFC) of stabilized chlorine dioxide rinse.

| Candida Species | MFC of stabilized chlorine dioxide rinse |
|---|---|
| C. albicans | 0.40% |
| C. dubliniensis | 0.40% |
| C. glabrata | 0.40% |
| C. krusei | 0.40% |

TABLE 3

Two replications of Time-kill after 30 seconds and 1 minute of stabilized chlorine dioxide oral rinse exposure against four Candida species (after 24 hours incubation). Growth control for each species was > 2000 CFU/mL.

| Candida Species | Concentration of rinse | Replicate 1 30 seconds | Replicate 1 1 minute | Replicate 2 30 seconds | Replicate 2 1 minute |
|---|---|---|---|---|---|
| C. albicans | 0.40% | 240 | 1020 | 20 | 20 |
|  | 0.80% | 0 | 0 | 0 | 0 |
| C. dubliniensis | 0.40% | >2000 | >2000 | >2000 | >2000 |
|  | 0.80% | 0 | 0 | 0 | 0 |
| C. glabrata | 0.40% | >2000 | >2000 | >2000 | >2000 |
|  | 0.80% | 0 | 0 | 0 | 0 |
| C. krusei | 0.40% | >2000 | >2000 | >2000 | >2000 |
|  | 0.80% | 0 | 0 | 0 | 0 |

TABLE 4

Time kill after 1-minute exposure of chlorhexidine gluconate against Candida species (after 24 hours incubation). Growth control for each species was > 2000 CFU/mL.

| Candida Species | Concentration of CHX | Bacteria Count (CFU/mL) |
|---|---|---|
| C. albicans | 0.015% | >2000 |
|  | 0.12% | >2000 |
| C. dubliniensis | 0.015% | >2000 |
|  | 0.12% | >2000 |
| C. glabrata | 0.015% | >2000 |
|  | 0.12% | >2000 |
| C. krusei | 0.015% | >2000 |
|  | 0.12% | >2000 |

We claim:

1. A method for treating candidiasis caused by at least one of *Candida glabrata* or *Candida krusei*, said method comprising:
   (a) administering to a person in need thereof fungistatic a composition of stabilized chlorine dioxide having a concentration of about 0.0004% to about 0.025% (w/v if a liquid or spray and w/g if a paste or gel); and
   (b) wherein at least one of cellular metabolism, function, or growth is inhibited in at least one of *Candida glabrata*, or *Candida krusei*.

2. The method of claim 1 wherein the composition is selected from an oral wash, a rinse, a dental soak, a paste, a gel, or a spray.

* * * * *